US010136807B2

(12) United States Patent
Tomatsu et al.

(10) Patent No.: US 10,136,807 B2
(45) Date of Patent: Nov. 27, 2018

(54) OPTICAL COHERENCE TOMOGRAPHY SYSTEM (71) Applicant: CANON KABUSHIKI KAISHA, Tokyo (JP)

(72) Inventors: Nobuhiro Tomatsu, Yokohama (JP); Stefan Zotter, Vienna (AT); Michael Pircher, Vienna (AT); Christoph Hitzenberger, Vienna (AT)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/104,555

(22) PCT Filed: Dec. 26, 2014

(86) PCT No.: PCT/JP2014/084762
§ 371 (c)(1),
(2) Date: Jun. 15, 2016

(87) PCT Pub. No.: WO2015/105034
PCT Pub. Date: Jul. 16, 2015

(65) Prior Publication Data
US 2016/0310002 A1 Oct. 27, 2016

(30) Foreign Application Priority Data
Jan. 10, 2014 (JP) .................. 2014-003700

(51) Int. Cl.
A61B 3/10 (2006.01)
G01B 9/02 (2006.01)
(Continued)

(52) U.S. Cl.
CPC ............ A61B 3/102 (2013.01); A61B 3/0025 (2013.01); A61B 3/14 (2013.01); G01B 9/02091 (2013.01);
(Continued)

(58) Field of Classification Search
CPC ......... A61B 3/102; A61B 3/14; A61B 3/0025; G01B 9/02091
See application file for complete search history.

(56) References Cited

U.S. PATENT DOCUMENTS 8,390,818 B2 3/2013 Hirose et al.
8,517,537 B2 8/2013 Suehira et al.
(Continued)

FOREIGN PATENT DOCUMENTS

EP 2 314 203 A1 4/2011
JP 2004-088129 A 3/2004
(Continued)

OTHER PUBLICATIONS

Stefan Zotter, et al., "Large-field high-speed polarization sensitive spectral domain in OCT and its applications in ophthalmology," Biomedical Optics Express, vol. 3, No. 11, Nov. 1, 2012, pp. 2720-2732.
(Continued)

Primary Examiner — Jack Dinh
(74) Attorney, Agent, or Firm — Fitzpatrick, Cella, Harper & Scinto (57) ABSTRACT In a polarization-sensitive optical coherence tomography system, an interferometer includes single mode fibers and a plurality of polarization controllers. At least one of the plurality of polarization controllers is disposed on each of the fibers of the interferometer. The fibers include a fiber for sample light beam, a fiber for reference light beam, and a fiber for detection light beam. An image forming unit determines a pixel value from a data set consists of two orthogonal polarization components simultaneously obtained at substantially identical spatial positions of a test sample, wherein a measurement light beam has static single polarization state.

17 Claims, 6 Drawing Sheets (51) Int. Cl.
*A61B 3/00* (2006.01)
*A61B 3/14* (2006.01)

(52) U.S. Cl.
CPC ...... *G01B 2290/45* (2013.01); *G01B 2290/70* (2013.01)

(56) References Cited

U.S. PATENT DOCUMENTS

| | | |
|---|---|---|
| 9,149,181 B2 | 10/2015 | Matsumoto et al. |
| 9,161,690 B2 | 10/2015 | Tomatsu et al. |
| 9,241,625 B2 | 1/2016 | Iwase et al. |
| 9,471,277 B2 | 10/2016 | Yasuno et al. |
| 9,717,409 B2 | 8/2017 | Iwase et al. |
| 2004/0239938 A1 | 12/2004 | Izatt |
| 2013/0188133 A1 | 7/2013 | Iwase et al. |
| 2014/0115022 A1 | 4/2014 | Yasuno et al. |
| 2016/0066784 A1 | 3/2016 | Yamazaki et al. |
| 2016/0100756 A1 | 4/2016 | Iwase et al. |

FOREIGN PATENT DOCUMENTS

| | | |
|---|---|---|
| JP | 2013-019773 A | 1/2013 |
| JP | 2013-146445 A | 8/2013 |
| WO | 2012/004970 A1 | 1/2012 |

OTHER PUBLICATIONS

Barry Cense, et al., "Polarization-sensitive spectral-domain optical coherence tomography using a single line scan camera," Optics Express, vol. 15, No. 5, Mar. 5, 2007, pp. 2421-2431.

Hermann Lin, et al., "All fiber optics circular-state swept source polarization-sensitive optical coherence tomography," Journal of Biomedical Optics, vol. 19, No. 2, Feb. 2014, pp. 021110-1-021110-9.

May 21, 2015 International Search Report and Written Opinion in International Patent Appln. No. PCT/JP2014/084762.

OPTICAL COHERENCE TOMOGRAPHY SYSTEM

TECHNICAL FIELD

The present invention relates to optical coherence tomography systems, particularly, to an optical coherence tomography system that can capture information on polarization characteristics of a target eye.

BACKGROUND ART

In these years, optical coherence tomography (OCT) systems (referred to as OCT systems, below) that utilize interference due to low coherence light have been practically used. The OCT systems can noninvasively capture a tomograph image of a test sample with high resolution. The OCT systems have thus been growing into indispensable systems, particularly in ophthalmology, to obtain a tomograph image of the ocular fundus of the target eye. Besides ophthalmology, the OCT systems are used for purposes such as for observing a tomograph of the skin or capturing a tomograph image of the wall surfaces of the digestive organ or the circulatory organ in the form of an endoscope or a catheter.

An ophthalmologic OCT system that can capture functional OCT images besides normal OCT images (also referred to as intensity images) has been developed where the normal OCT images image the shape of ocular fundus tissues while the functional OCT images image optical characteristics, actions, or other information of ocular fundus tissues. Particularly, polarization-sensitive OCT systems that can draw a nerve fiber layer or a retinal layer have been developed as one of functional OCT systems and the systems for diseases such as glaucoma or age-related macular degeneration have been increasingly studied.

A polarization-sensitive OCT system can form a polarization OCT image using a polarization parameter (retardation and orientation), which is one of optical characteristics of ocular fundus tissues, to discriminate or segment the ocular fundus tissues. Generally, a polarization-sensitive OCT system includes an optical system in which a wave plate (for example, λ/4 wave plate or λ/2 wave plate) is used to appropriately change the polarization states of light measured by the OCT system and reference light. A polarization-sensitive OCT system forms a polarization OCT image by controlling polarization of light emitted from a light source, using light that has been modulated into a desired polarization state as a measurement light beam for observing a specimen, splitting an interference light beam into two orthogonal straight polarized light beams, and detecting the polarized light beams (NPL 1: Biomedical Optics Express 3 (11), Stefan Zotter et al. "Large-field high-speed polarization sensitive spectral domain OCT and its applications in ophthalmology").

As a method for controlling polarization, a method for modulating a polarized state using an electro-optic modulator (EOM) has been provided (NPL 2: Optics Express 5 (15), Barry Cense et al. "Polarization-sensitive spectral-domain optical coherence tomography using a single line scan camera"). This method enables formation of polarization OCT images on the basis of polarization information of multiple polarized states by applying light beams of multiple polarized states to the same position, whereby more accurate polarization OCT images can be captured.

Meanwhile, size reduction of OCT systems is required at medical institutions with the needs of installing various inspection devices. Thus, a polarization-sensitive OCT system that is smaller than and has a more flexible optical system than existing systems by including an optical fiber as an optical system has been developed (NPL 3: Journal of Biomedical Optics 19 (2), Hermann Lin et al. "All fiber optics circular-state swept source polarization-sensitive optical coherence tomography").

Existing polarization-sensitive OCT systems include components such as a polarization maintaining (PM) fiber (referred to as a PM fiber, below), a wave plate, and an EOM for controlling polarization. Components such as PM fibers, wave plates, and EOMs, however, are extremely expensive and consequently make the polarization-sensitive OCT expensive. Moreover, conventional OCT systems are unable to easily accept additional components and an additional polarization-OCT-image capturing function. Thus, medical institutions that have already had a conventional OCT system have to purchase a new system, causing a heavy burden. Furthermore, a large space is required to install two OCT systems.

NPL 1 discloses the configuration of a polarization-sensitive OCT system that includes an interferometer for which a PM fiber is used and a wave plate for controlling polarization of a measurement light beam and a reference light beam. This OCT system can facilitate polarization adjustment but cannot be formed at a low cost due to the use of expensive optical elements.

NPL 2 discloses a polarization-sensitive OCT system including an EOM for controlling polarization. However, as in the system of NPL 1, the polarization-sensitive OCT system cannot be formed at a low cost because of a very expensive EOM.

NPL 3 discloses a polarization-sensitive OCT system including an interferometer for which a PM fiber is used. The use of the PMF reduces the size of the system but prevents cost reduction of the system because the PMF is a very expensive optical component.

In addition, the polarization-sensitive OCT systems of the above-described NPLs have configurations basically different from the configuration of conventional OCT systems and thus conventional OCT systems are highly unlikely to be extensible, specifically, to be changed into polarization-sensitive OCT systems. Changing conventional OCT systems into the above-described polarization-sensitive OCT systems involves replacement or addition of most of the components, making it impossible to easily add functions. Consequently, a polarization-sensitive OCT system is installed along with a conventional OCT system, preventing space saving.

SUMMARY OF INVENTION

In view of these problems, one embodiment of the present invention provides a polarization-sensitive OCT system that can be formed in a small size at a low cost. Furthermore, one embodiment of the present invention provides a polarization-sensitive OCT system that can easily add a polarization-OCT-capturing function to a conventional OCT system.

According to one aspect of the present invention, there is provided an optical coherence tomography system that includes the following configuration: an interferometer includes single mode fibers and a plurality of polarization controllers, at least one of the plurality of polarization controllers is disposed on each of the fibers of the interferometer, which include a fiber for a measurement light beam, a fiber for a reference light beam, and a fiber near a detector, and an image forming unit determines a pixel value from a data set including two orthogonal polarization components concurrently obtained at substantially identical spatial positions of a test sample, wherein a measurement light beam has static single polarization state.

According to another aspect of the present invention, there is provided a polarization-sensitive optical coherence tomography apparatus comprising: a plurality of single mode fibers; a first polarization control means for controlling polarization state of measurement light; a second polarization control means for controlling polarization state of a mixed light generated by mixing a light returned from a test sample and a reference light corresponding to the measurement light, wherein the light returned from the test sample is obtained by applying the measurement light to the test sample through an optical system comprising the plurality of single mode fibers, the measurement light having a polarization state controlled by the first polarization control means; and detecting means for detecting the mixed light having a polarization state controlled by the second polarization control means, for each polarization component.

One aspect of the present invention allows a polarization-sensitive OCT system to be formed in a small size at a low cost. In addition, one aspect of the present invention facilitates addition of a polarization OCT function to a conventional OCT system.

Further features of the present invention will become apparent from the following description of exemplary embodiments with reference to the attached drawings.

BRIEF DESCRIPTION OF DRAWINGS

The accompanying drawings, which are incorporated in and constitute a part of the specification, illustrate embodiments of the invention and, together with the description, serve to explain the principles of the invention.

DESCRIPTION OF EMBODIMENTS

An embodiment of the present invention is described in detail referring to the drawings.

First Embodiment

A configuration of a polarization-sensitive OCT system according to the embodiment will be described referring to FIG. 1.

[Entire Configuration of System]

Figure 1:
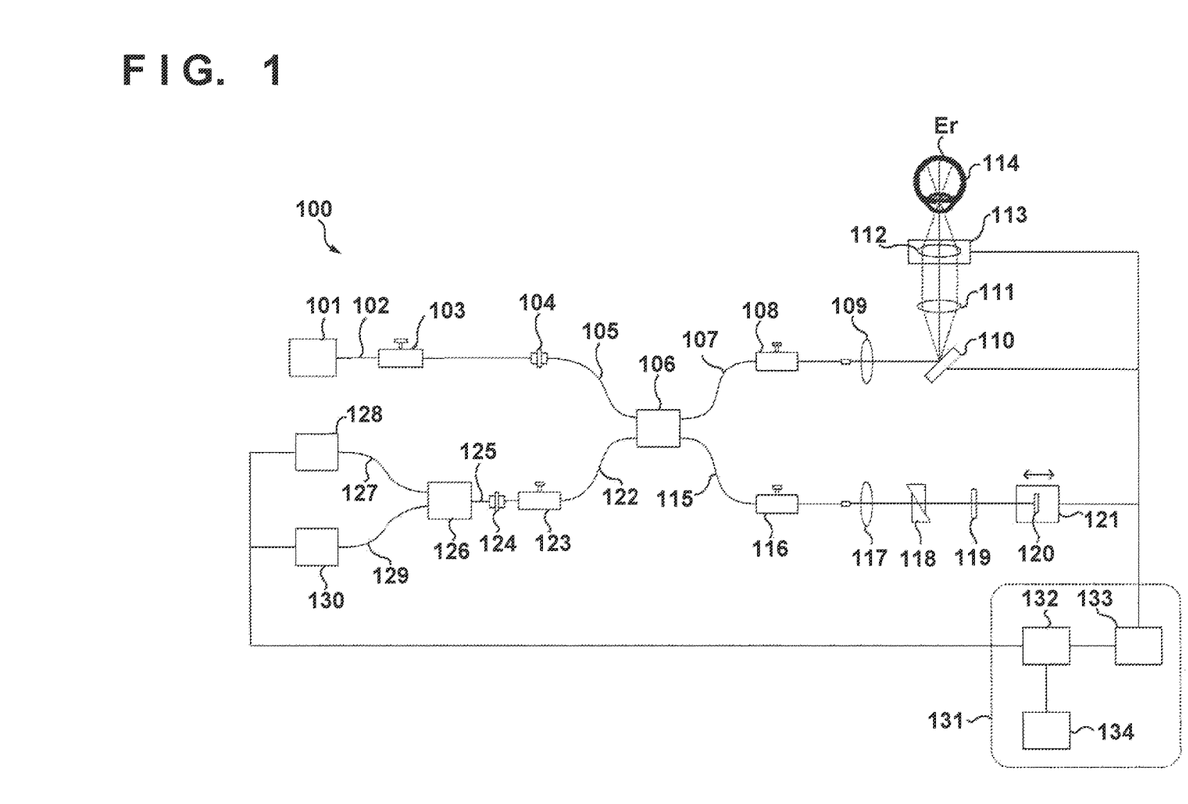
FIG. 1 is a schematic diagram of the entire configuration of a polarization-sensitive OCT system according to a first embodiment.

FIG. 1 is a schematic diagram of the entire configuration of the polarization-sensitive OCT system according to the embodiment. In this embodiment, the configuration of a spectral domain (SD)-OCT system is described.

<Configuration of Polarization-Sensitive OCT System 100>

The Polarization-Sensitive OCT System 100 according to the first embodiment includes a plurality of single mode fibers and a plurality of polarization controllers, wherein at least one of the plurality of polarization controllers is disposed on each of the fibers of the interferometer, which include a fiber (107) for a measurement light beam, a fiber (115) for a reference light beam, and a fiber (122) near a detector. An image forming unit (132) determines a pixel value from a data set including two orthogonal polarization components concurrently obtained at substantially identical spatial positions of the test sample (114). A measurement light beam has static single polarization state. The configuration of a polarization-sensitive OCT system 100 will be described in detail now.

A light source 101 is a super luminescent diode (SLD) light source, which is a low coherent light source, and emits a light beam having, for example, a center wavelength of 850 nm and a band width of 50 nm. Although a SLD is used as the light source 101, any light sources that can emit a low coherent light beam, such as an amplified spontaneous emission (ASE) light source, may be used.

A light beam emitted from the light source 101 passes through a single mode fiber (referred to as an SM fiber, below) 102, a polarization controller 103, a connector 104, and an SM fiber 105 and is guided to a beam splitter 106, at which the light beam is split into a measurement light beam (also referred to as an OCT measurement light) and a reference light beam (also referred to as a reference light beam corresponding to the OCT measurement light). The beam splitter 106 is an example of dividing means. The ratio of the reference light beam to the measurement light beam at the beam splitter 106 is 90:10. Although the ratio of the reference light beam to the measurement light beam at the beam splitter 106 is 90:10 in this embodiment, it is not limited to this. The splitting ratio of the beam splitter 106 may be set to other value so that signal to noise ratio of the OCT system is optimized. The polarization controller 103 can change the polarization of light emitted from the light source 101 to a desired polarization state. In this embodiment, the polarization controller 103 adjusts the light in such a manner that the light is linearly polarized. Although not described in this embodiment, when the light source 101 does not polarize light to a large degree, a polarizer may be disposed between the polarization controller 103 and the connector 104 to increase the degree of polarization to which the light emitted from the light source 101 is polarized. In this case, the amount of light that passes through the polarizer can be adjusted by adjusting the polarization controller 103. Alternatively, a configuration may only include a polarizer on the SM fiber 102 instead of the polarization controller 103. In this case, only the degree of polarization to which the light emitted from the light source 101 is polarized can be increased without the need for adjusting the polarization state of the emitted light. However, whether the amount of light is sufficient has to be checked since the amount of light guided to the interferometer may become short depending on the polarization state of the light.

The split measurement light beam is emitted through an SM fiber 107 and changed into a parallel light beam by a collimator 109. A polarization controller 108, which is an example of first polarization control means, disposed at a portion on the SM fiber 107, can appropriately change the polarization state of the emitted measurement light beam. In this embodiment, the polarization controller 108 alters the polarization state to a circularly polarized light beam incident on the sample. The measurement light beam changed into a parallel light beam enters a target eye 114 as a test sample via a galvano scanner 110, which scans an ocular fundus Er of the target eye 114 with the measurement light beam, a scan lens 111, and a focus lens 112. Here, the galvano scanner 110 is described as being a single mirror, but two galvano scanners may be provided so as to raster scan the ocular fundus Er of the target eye 114. Although we use the galvano scanners in this embodiment, it is not limited to this. For example, polygon scanners, resonant scanners, MEMS mirrors are usable. The focus lens 112, fixed onto a stage 113, is capable of focus adjustment by moving in the optical axis direction. The galvano scanner 110 and the stage 113 are controlled by a drive controller 133, so that a desired range of the ocular fundus Er of the target eye 114 (also referred to as a tomography-image capturable range, a tomography-image capturable portion, or a measurement-light applied portion) can be scanned with the measurement light beam.

The measurement light beam enters the target eye 114 via the focus lens 112 on the stage 113 and is focused on the ocular fundus Er. The measurement light beam that has been applied to the ocular fundus Er is reflected and scattered by each retinal layer and is returned to the beam splitter 106 through the above-described optical path.

On the other hand, the reference light beam split by the beam splitter 106 is emitted through an SM fiber 115 and changed into a parallel light beam by a collimator 117. A polarization controller 116, disposed at a portion on the SM fiber 115, can appropriately change the polarization state of the reference light beam. In this embodiment, the reference light beam is in a linearly polarized state at the entrance to the polarizing beam splitter 126 which is an example of polarization dividing means, the orientation of the linear polarization orientation being inclined at 45° to each of the orthogonal polarization axes of the polarizing beam splitter 126. Although the polarization state of the reference beam is linear in this embodiment, other polarization states are possible, e.g. elliptic, with the axis of the ellipse being inclined at 45°. The reference light beam passes through a dispersion compensating glass 118 and a ND filter 119, is reflected off a mirror 120 on a coherence gate stage 121, and is returned to the beam splitter 106. The coherence gate stage 121 is controlled by the drive controller 133 so as to allow for variations in axial length of the eye of a subject or other variations.

The measurement light beam and the reference light beam returned to the beam splitter 106 are mixed and become an interference light beam, which enters a polarization beam splitter 126 through an SM fiber 122, a polarization controller 123 which is an example of second polarization control means, a connector 124, and an SM fiber 125. At the polarization beam splitter 126, the interference light beam is split into two light beams, that is, a vertical polarization component (referred to as a V polarization component, below) and a horizontal polarization component (referred to as an H polarization component) in accordance with the two orthogonal polarization axes. The V component of the split interference light beam enters the detector 128 through the SM fiber 127, while the H component of the split interference light beam enters the detector 130 through the SM fiber 129. The light beams received by each of the detectors 128 and 130 are output as electric signals and received by a signal processor 132.

In this embodiment, the light beam is equivalently split into the V polarization component and the H polarization component because the reference light beam is linearly polarized at 45°. Since the measurement light beam is changed into the circularly polarized light beam in this embodiment, data on the ocular fundus Er of the target eye 114 can be simultaneously obtained regardless of the cells or the direction of fibers of the ocular fundus Er. Consequently, data on the ocular fundus Er for all the polarization directions can be collectively obtained at once, whereby data can be obtained by only a single image capturing operation for a given sample position without performing multiple image capturing operations for different polarization directions.

Referring now to FIGS. 1 to 4, how the polarization controllers 108, 116, and 123 control the polarization state will be described.

Figure 2:
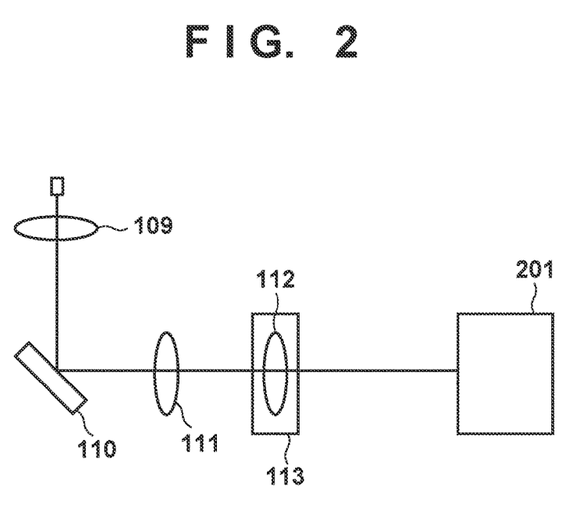
FIG. 2 is an illustration relating to a method for adjusting the polarization state according to the first embodiment.

Firstly, the polarization controller 108 controls the polarization state of light entering the target eye 114. The incident light entering the target eye 114 has static single polarization state and not changed temporally. In this embodiment, the measurement light beam linearly polarized by the polarization controller 103 is altered by the polarization controller 108 into a circularly polarized light beam. A polarimeter 201 is placed behind the focus lens 112 and the polarization controller 108 is adjusted in a manner such that the polarimeter 201 detects circular polarization (FIG. 2). Here, a detector such as a polarimeter is used for confirming the polarization state, but the polarization state may be confirmed by using other components, such as an optical power meter and a polarizer or a wave plate. The light beam entering to the target eye 114 is circularly polarized in this embodiment; however the present invention is not limited to. The polarization state can be elliptically polarized.

Figure 3A:
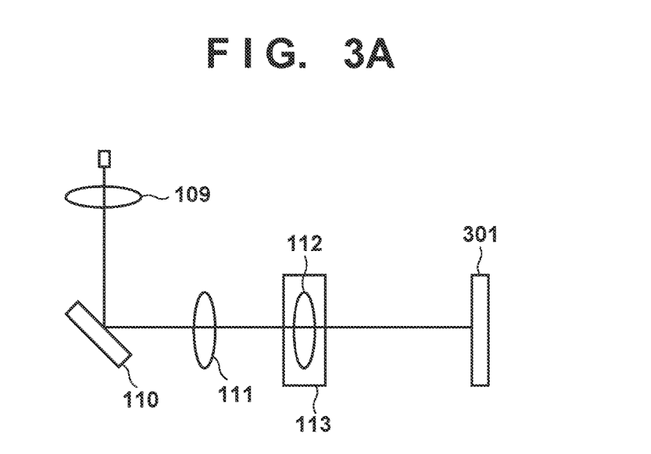
FIGS. 3A and 3B are illustrations relating to a method for adjusting the polarization state according to the first embodiment.
Figure 3B:
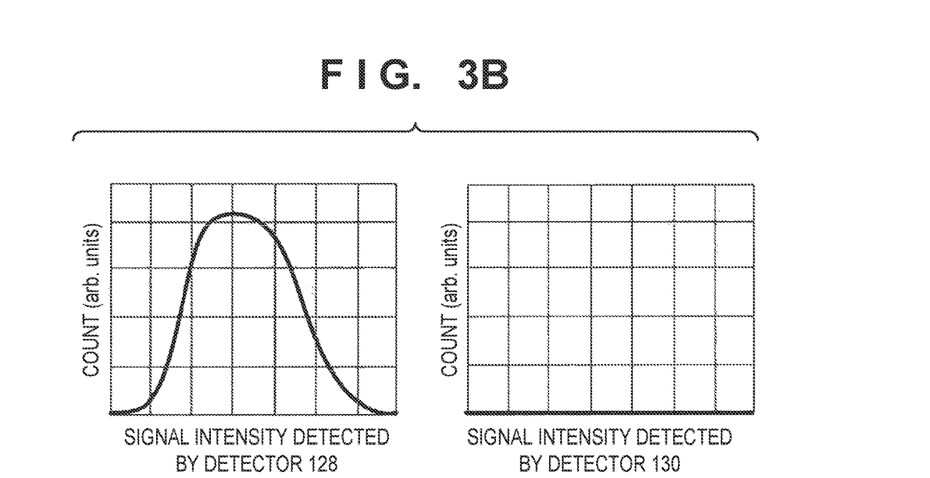

Subsequently, the polarization controller 123 is adjusted. The polarization controller 123 is adjusted using only the measurement light beam. A mirror 301 is placed behind the focus lens 112 and the angle of the mirror 301 is adjusted in a manner such that light emitted through the SM fiber 107 is guided to the mirror 301 via the collimator 109, the galvano scanner 110, and lenses 111 and 112 and then reflected by the mirror 301 to be returned to the beam splitter 106 (FIG. 3A). The measurement light beam that has entered the beam splitter 106 passes through the SM fiber 122, the polarization controller 123, the connector 124, and the SM fiber 125 and is guided to the polarization beam splitter 126. The light beam is split into two polarization components, which are the V polarization component and the H polarization component, at the polarization beam splitter 126. The spectral distribution of light intensity detected by the detectors 128 and 130 is displayed on a display 134 and the polarization controller 123 is adjusted so that the light beam is linearly polarized at the polarization beam splitter 126 and only one of the detectors 128 and 130 detects the light (FIG. 3B).

Figure 4:
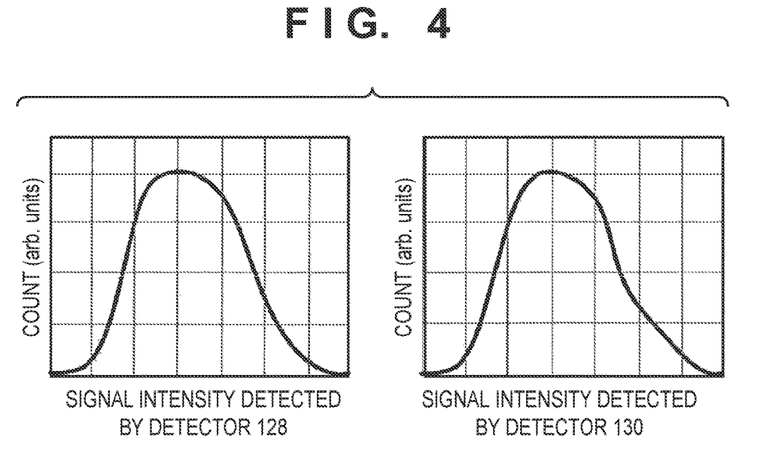
FIG. 4 is an illustration relating to a method for adjusting the polarization state according to the first embodiment.

Finally, the polarization controller 116 is adjusted. The polarization controller 116 is adjusted using only the reference light beam. The reference light beam passes through the SM fiber 115, the polarization controller 116, the collimator 117, the dispersion compensating glass 118, and the ND filter 119 and is reflected by the mirror 120 to be guided back to the beam splitter 106. Here, the polarization controller 116 is adjusted so that the amounts of light detected by the detectors 128 and 130 become substantially the same (FIG. 4). Consequently, the reference light beam guided to the polarization beam splitter can be linearly polarized in a manner such that the ratio of the V polarization component to the H polarization component is 1:1, that is, linearly polarized so as to be inclined at 45° with respect to the two orthogonal polarization axes. The reference light beam has single polarization state and not changed temporally.

<Controller 131>

The controller 131 for controlling the entire system will be described.

The controller 131 includes the drive controller 133, the signal processor 132, and the display 134. The drive controller 133 controls each component in the above-described manner.

The signal processor 132 forms an image, analyses the formed image, and forms visualized information of the analytical results on the basis of signals output from the detectors 128 and 130. For example, the signal processor 132 forms an image of the test sample (the target eye 114) on the basis of a degree of depolarization, or forms an image of the test sample (the target eye 114) on the basis of a change in phase. The method for forming an image and the method for analyzing the formed image are the same as those described in NPL 1 and thus are not described here.

An image formed by or results analyzed by the signal processor 132 are displayed on a display screen of the display 134 (for example, a display made of liquid crystal or the like). Image data formed by the signal processor 132 may be transmitted to the display 134 in a wired or wireless manner.

Although the display 134 and other members are included in the controller 131, the present invention is not limited to this configuration and the display 134 and other members may be provided separately from the controller 131. In that case, it is preferable that a display have a touch-panel function, with which the position at which an image is displayed on the touch panel is movable, the image can be enlarged or contracted, an image displayed on the touch panel is switchable, or other operations can be made.

In the configuration described above, the polarization state is appropriately set by the polarization controllers disposed on the optical paths of the interferometer. Thus, a polarization-sensitive OCT system can be formed at a low cost by using a reasonable SM fiber, not an expensive PM fiber. Although the case of an SD-OCT is described in this embodiment, the present invention is not limited to this case. A polarization OCT image can be similarly formed even by an SS-OCT, structured using a swept source (SS) light source (SS light source, below), if the SS-OCT is formed into a similar configuration. That is, a swept light source can be used as the light source 101. In this embodiment, the Michelson interferometer is used but the use of the Mach-Zehnder interferometer would bring about similar effects. Although this embodiment does not include any polarizer, a polarizer may be provided between the SM fiber 102 and the SM fiber 105 depending on the degree of polarization to which the light source polarizes light. In such a case, the connector 104 is removed from the SM fibers 102 and 105 and an input terminal of the polarizer is connected to the SM fiber 102, while an output terminal of the polarizer is connected to the SM fiber 105. Thus, an alternative configuration can be made. Here, the method for directly connecting the SM fibers 102 and 105 and a polarizer is described, but the present invention is not limited to this method. When a component in which an optical fiber and a polarizer are integrated is to be added to the system, a polarizer can be added by removing the SM fiber 102 from the connector 104, connecting a polarizer input-side optical fiber to the SM fiber 102 using a new connector, and connecting a polarizer output-side optical fiber to the connector 104.

Second Embodiment

In this embodiment, referring to FIGS. 5 and 6, a method for forming a polarization-sensitive OCT system by adding components to a conventional OCT system will be described. In this embodiment, an SS-OCT is used for a light source 501, as an example. Since the basic configuration of an SS-OCT is a publicly-known configuration, the SS-OCT is not described in detail here.

<Addition of Components to conventional OCT System>

Figure 5:
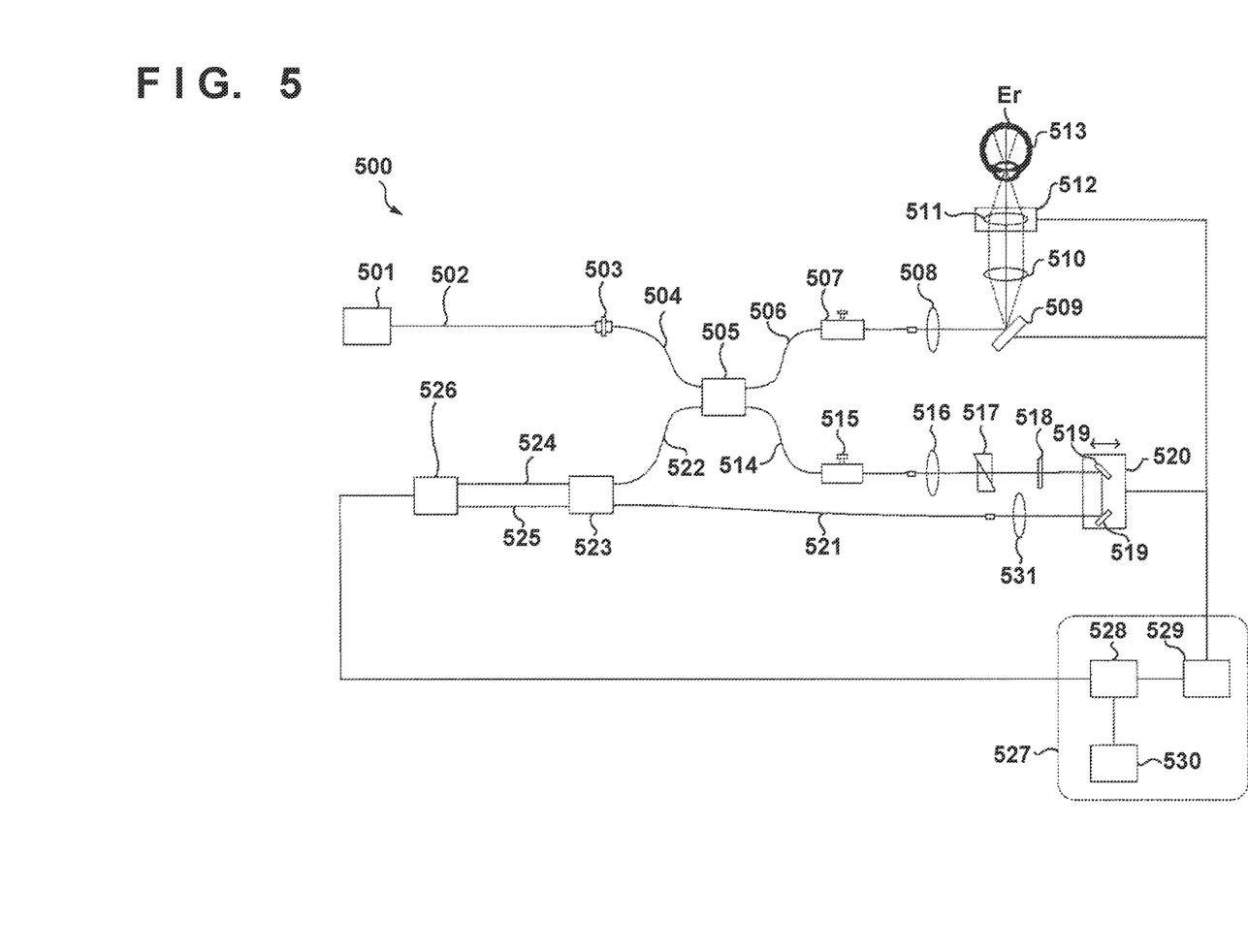
FIG. 5 is a schematic diagram of the entire configuration of a conventional OCT system according to a second embodiment.
Figure 6:
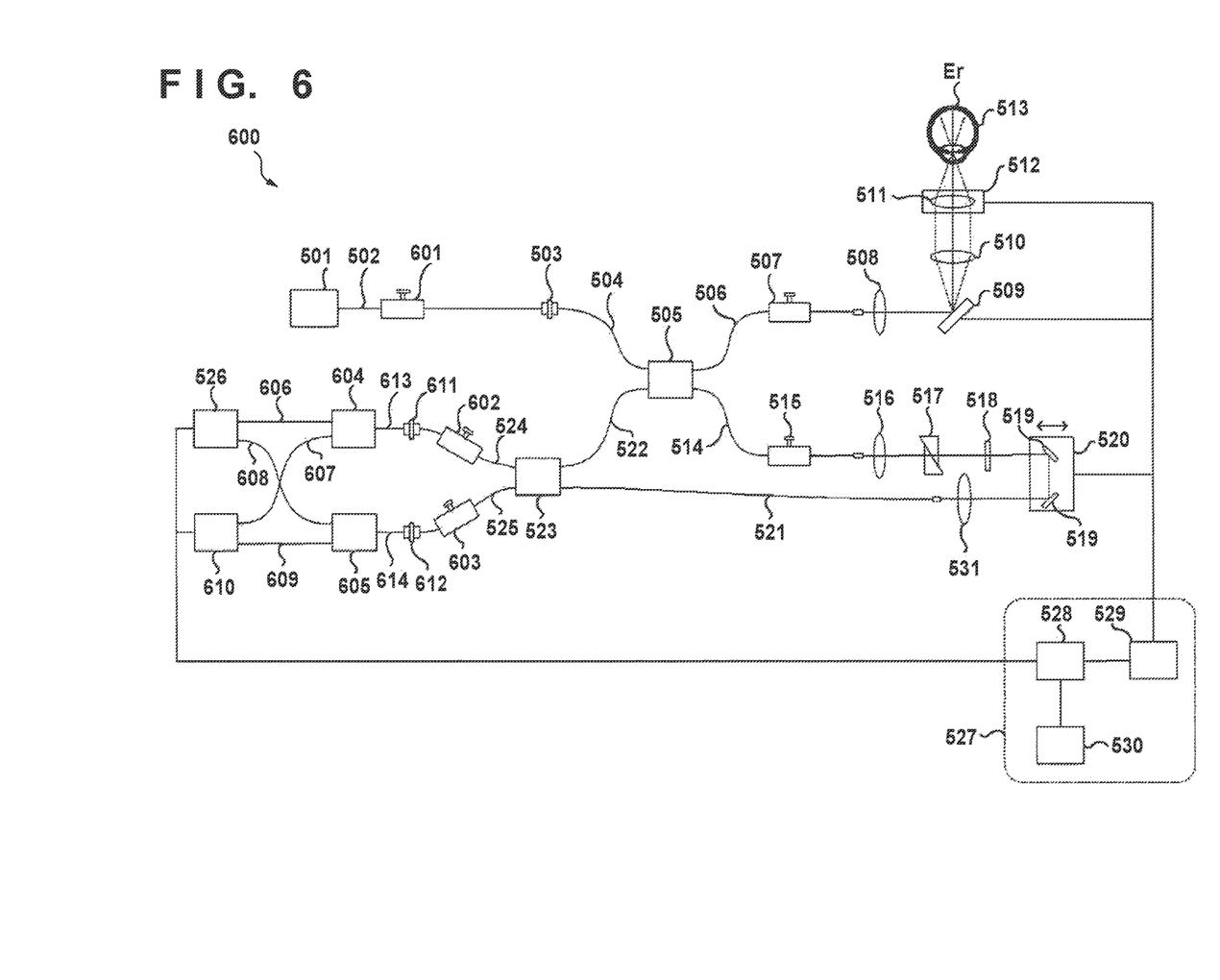
FIG. 6 is a schematic diagram of the entire configuration of a conventional OCT system that has been changed into a polarization OCT system according to the second embodiment.

FIG. 5 illustrates a conventional SS-OCT system. The configuration shown by reference numerals 503 to 518, 520 and 527 to 530 in FIG. 5 are similar to the configuration shown by reference numerals 104 to 119, 121 and 131 to 134 in FIG. 1 respectively. In FIG. 5, 519 are mirrors, 521, 524 and 525 are SM fibers, 523 is a polarization beam splitter as an example of polarization dividing means, 526 is a detector and 531 is a collimator. A detector 526 and SM fibers 524 and 525 are detachable from each other. Additional components are attached only to a portion on an SM fiber 502, which guides light emitted from a light source 501 to an interferometer, and a detector that detects an interference light beam.

Firstly, a polarization controller 601 is disposed at a portion on the optical fiber 502. Thus, the light emitted from the light source can be linearly polarized (FIG. 6).

Because polarization controller changes polarization state by clipping both sides of the fiber in general, it can be installed without detaching the SM fibers.

Then, polarization controllers 602 and 603 which are an example of the second polarization control means, polarization beam splitters 604 and 605, SM fibers 606, 607, 608, 609, 613, and 614, a detector 610, and connectors 611 and 612 are added to the detector that detects an interference light beam.

Firstly, the SM fibers 524 and 525 are removed from the detector 526 and respectively connected to the connectors 611 and 612. At this time, the polarization controllers 602 and 603 are respectively disposed on the SM fibers 524 and 525.

Subsequently, the SM fibers 613 and 614 are respectively connected to the connectors 611 and 612. Other ends of the SM fibers 613 and 614 are respectively connected to the polarization beam splitters 604 and 605.

Thereafter, the SM fiber 606 is connected in such a manner that an interference light beam emitted from the polarization beam splitter 604 enters the detector 526. In addition, the SM fiber 607 is connected in such a manner that another interference light beam emitted from the polarization beam splitter 604 enters an additional detector 610. Similarly, the SM fiber 608 is connected in such a manner that an interference light beam emitted from the polarization beam splitter 605 enters the detector 526. In addition, the SM fiber 609 is connected in such a manner that another interference light beam emitted from the polarization beam splitter 605 enters the detector 610.

At this time, the SM fibers 606, 607, 608, and 609 are connected in such a manner that the detectors 526 and 610 receive light having different polarization components. For example, the SM fibers 606 and 608 are connected in such a manner that, when a V polarization component split by the polarization beam splitter 604 enters the detector 526 through the SM fiber 606, the V polarization component split by the polarization beam splitter 605 enters the detector 526 through the SM fiber 608. Similarly, the SM fibers 607 and 609 are connected in such a manner that, an H polarization component split by the polarization beam splitter 604 enters the detector 610 through the SM fiber 607 and the H polarization component split by the polarization beam splitter 605 enters the detector 610 through the SM fiber 609.

By adding and connecting components in the above-described manner, a conventional OCT system can be changed into a polarization-sensitive OCT system that can form a polarization OCT image.

In this embodiment, the method for sequentially connecting components to the detector of the interferometer is described. However, a configuration in which components from the connectors 611 and 612 to the detectors 526 and 610 are integrated into a unit so as to be collectively detachable is more preferable.

In that case, conventional SS-OCT system can be changed to polarization-sensitive OCT system easily, only by connecting the fibers 524 and 525 to the connectors 611 and 612 which are components of the unit. The interference light beam is formed and split into two parts at the beam splitter 523, which are respectively guided to the polarization beam splitters 604 and 605 through the SM fibers 524 and 525. The split parts of the interference light beam are interference light components having opposite phases (referred to as a positive component and a negative component, below). The positive part of the split interference light beam is further guided to the polarization beam splitter 604, at which it is split into a positive H polarization component and a positive V polarization component. Similarly, the negative part of the split interference light beam is split into a negative H polarization component and a negative V polarization component at the polarization beam splitter 605. The positive H polarization component generated at the polarization beam splitter 604 and the negative H polarization component generated at the polarization beam splitter 605 respectively pass through the SM fibers 606 and 608 and are guided to the detector 526, at which the differential is detected. On the other hand, the positive V polarization component generated at the polarization beam splitter 604 and the negative V polarization component generated at the polarization beam splitter 605 pass through the SM fibers 607 and 609 and are guided to the detector 610.

Subsequently, polarization state of the light beam is adjusted using the polarization controllers 507 (an example of the first polarization control means), 515, 602 and 603. In the SS-OCT 500, the reference light beam and the sample light beam need to be adjusted to same polarization state so that strength of interference light beam at the beam splitter 523 becomes as high as possible.

However, the polarization state of the light beam entering to the target eye 513 needs to be circularly polarized in the polarization-sensitive OCT. In addition, H and V polarization components of the reference light beam need to have equal strength to each other. Therefore, polarization state adjustment described in the first embodiment is applied.

Interference signals detected by the detectors 526 and 610 are converted into electric signals and transmitted to a signal processor 528. The signal processor 528 forms a polarization OCT image on the basis of information from the detectors. The method for forming polarization OCT images is not described here since the method has been described in NPL 1.

In the above-described manner, a conventional OCT system can be easily changed into a polarization-sensitive OCT system that can form polarization OCT images. In the embodiment, an SS-OCT is described as an example. The present invention, however, is not limited to this configuration. An SD-OCT can be similarly changed into a polarization-sensitive OCT system that can form polarization OCT images by detaching and adding components in the similar manner. Specifically, by making a spectroscope, which is a detector, detachable, the alternative system can have the effects similar to those in the embodiment. In this embodiment, the Mach-Zehnder interferometer is used as an example, but the use of the Michelson interferometer would bring about similar effects. Although all the fibers are SM fibers in this embodiment, PM fibers may be partially used as needed. Although the embodiment does not include a polarizer, a polarizer may be disposed between the polarization controller 601 and a connector 503 depending on the degree of polarization to which the light source polarizes light.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-003700, filed Jan. 10, 2014, which is hereby incorporated by reference herein in its entirety.

The invention claimed is:

1. A polarization-sensitive optical coherence tomography system comprising:
   an interferometer which includes single mode fibers and a plurality of polarization controllers, wherein at least one of the plurality of polarization controllers is disposed on each of the fibers of the interferometer, which include a fiber for a sample light beam, a fiber for a reference light beam, and a fiber for a detection light beam; and
   an image forming unit which determines a pixel value from a data set consisting of two orthogonal polarization components simultaneously obtained at substantially identical spatial positions of an object,
   wherein a measurement light beam has a static single polarization state.

2. The polarization-sensitive optical coherence tomography system according to claim 1, wherein the static singular polarization state is a circular polarization state.

3. The polarization-sensitive optical coherence tomography system according to claim 1, wherein another polarization controller is disposed between a light source and a beam splitter.

4. The polarization-sensitive optical coherence tomography system according to claim 3, wherein a polarizer is disposed between the beam splitter and the polarization controller disposed between the light source and the beam splitter.

5. The polarization-sensitive optical coherence tomography system according to claim 1, wherein the interferometer is a Mach-Zehnder interferometer or a Michelson interferometer.

6. The polarization-sensitive optical coherence tomography system according to claim 1, wherein the image forming unit forms an image of the object on the basis of a polarization scrambling.

7. The polarization-sensitive optical coherence tomography system according to claim 1, wherein the image forming unit forms an image of the object on the basis of a change in phase.

8. The polarization-sensitive optical coherence tomography system according to claim 1, wherein a detector of the interferometer is detachable.

9. The polarization-sensitive optical coherence tomography apparatus according to claim 1, wherein the polarization controller disposed on the fiber for the sample light beam is adjusted such that the polarization state of the measurement light beam becomes the static single polarization state.

10. The polarization-sensitive optical coherence tomography apparatus according to claim 9, wherein after the polarization controller disposed on the fiber for the sample light beam has been adjusted, the polarization controller disposed on the fiber for the detection light beam is adjusted such that intensities of lights of the two orthogonal polarization components become substantially the same.

11. A polarization-sensitive optical coherence tomography apparatus comprising:
a plurality of single mode fibers;
a first polarization control unit configured to control a polarization state of a measurement light;
a second polarization control unit configured to control a polarization state of a combined light generated by combining (i) a light returned from an object and (ii) a reference light corresponding to the measurement light, wherein the light returned from the object is obtained by applying the measurement light to the object through an optical system comprising the plurality of single mode fibers, the measurement light having a polarization state controlled by the first polarization control unit; and
a detecting unit configured to detect the combined light having a polarization state controlled by the second polarization control unit, for each polarization component.

12. The polarization-sensitive optical coherence tomography apparatus according to claim 11, further comprising a polarization dividing unit configured to divide the combined light into a plurality of lights of different polarization components,
wherein the second polarization control unit controls each of the plurality of lights, and
wherein the detecting unit detects each of the plurality of lights, wherein each polarization state of the plurality of lights is controlled by the second polarization control unit.

13. The polarization-sensitive optical coherence tomography apparatus according to claim 11, where the first polarization control unit controls a polarization state of the measurement light to a circular polarization state.

14. The polarization-sensitive optical coherence tomography apparatus according to claim 11, further comprising:
a swept source light source; and
a dividing unit configured to divide a light from the swept source light source into the measurement light and the reference light.

15. The polarization-sensitive optical coherence tomography apparatus according to claim 11, wherein the detecting unit detects a light returned from a mirror provided in a measurement optical path, and
wherein each polarization state of the plurality of lights is controlled by the second polarization control unit based on the returned light detected by the detecting unit.

16. A method for adjusting a polarization-sensitive optical coherence tomography apparatus that comprises (a) a plurality of single mode fibers, (b) a first polarization controller configured to control a polarization state of a measurement light, and (c) a second polarization controller configured to control a polarization state of a combined light via an optical system comprising the plurality of single mode fibers, the combined light being generated by combining (i) a light returned from an object irradiated with the measurement light and (ii) a reference light corresponding to the measurement light, the method comprising:
adjusting the first polarization controller such that the polarization state of the measurement light becomes a static single polarization state; and
adjusting, after a polarization controller disposed on a fiber for a sample light beam has been adjusted, the second polarization controller such that intensities of lights of orthogonal polarization components that are different from each other become substantially the same.

17. A non-transitory computer-readable storage medium storing a program for causing a computer to execute a method for adjusting a polarization-sensitive optical coherence tomography apparatus that comprises (a) a plurality of single mode fibers, (b) a first polarization controller configured to control a polarization state of a measurement light, and (c) a second polarization controller configured to control a polarization state of a combined light via an optical system comprising the plurality of single mode fibers, the combined light being generated by combining (i) a light returned from an object irradiated with the measurement light and (ii) a reference light corresponding to the measurement light, the method comprising:
adjusting the first polarization controller such that the polarization state of the measurement light becomes a static single polarization state; and
adjusting, after a polarization controller disposed on a fiber for a sample light beam has been adjusted, the second polarization controller such that intensities of lights of orthogonal polarization components that are different from each other become substantially the same.

* * * * *